(12) United States Patent
Spain

(10) Patent No.: US 6,696,265 B1
(45) Date of Patent: Feb. 24, 2004

(54) SYSTEM AND METHOD FOR ELIMINATING THE EFFECTS OF DOUBLETS AND CARRYOVER

(75) Inventor: Michael D. Spain, Austin, TX (US)

(73) Assignee: Luminex Corporation, Austin, TX (US)

( * ) Notice: Subject to any disclaimer, the term of this patent is extended or adjusted under 35 U.S.C. 154(b) by 0 days.

(21) Appl. No.: 09/641,401

(22) Filed: Aug. 17, 2000

Related U.S. Application Data

(60) Provisional application No. 60/149,226, filed on Aug. 17, 1999.

(51) Int. Cl.[7] ............................. G01N 33/53; C12Q 1/68
(52) U.S. Cl. ........................... 435/7.92; 435/6; 435/7.1; 435/7.93; 435/7.94; 436/517; 436/518; 436/523; 436/524; 436/525; 436/526; 436/527; 436/528; 436/529; 436/530; 436/531; 436/532; 436/533; 436/534; 436/535; 436/536

(58) Field of Search ..................... 435/6, 7.1, 7.92, 435/7.93, 7.94, 973; 436/517, 518, 523–535, 538, 63, 546, 165, 166, 172, 177

(56) References Cited

U.S. PATENT DOCUMENTS

| | | | | |
|---|---|---|---|---|
| 4,665,020 A | * | 5/1987 | Saunders | 435/7 |
| 5,229,265 A | * | 7/1993 | Tometsko | 435/6 |
| 5,606,164 A | * | 2/1997 | Price et al. | 250/399.09 |
| 5,837,547 A | * | 11/1998 | Schwartz | 436/10 |
| 5,981,180 A | * | 11/1999 | Chandler et al. | 435/6 |

* cited by examiner

Primary Examiner—Christopher L. Chin
Assistant Examiner—Gailene R. Gabel
(74) Attorney, Agent, or Firm—Gilberto M. Villacorta; Robert R. Seabold; Katten Muchin Zavis Rosenman

(57) ABSTRACT

The present invention relates to the substantial elimination of errors attributable to carryover microspheres, doublets, or misclassification of microsphere subsets. The present invention is based upon passing a sufficient minimum number microspheres through the flow analyzer during an assay run.

7 Claims, No Drawings

SYSTEM AND METHOD FOR ELIMINATING THE EFFECTS OF DOUBLETS AND CARRYOVER

CROSS-REFERENCE TO RELATED APPLICATION

The present application claims the benefit of the priority date of co-pending provisional patent application Ser. No. 60/149,226, filed Aug. 17, 1999, the complete disclosure of which is incorporated by reference herein.

FIELD OF THE INVENTION

This invention relates to statistical methods of eliminating the effects of doublets and carryover from sample to sample in a flow analysis system.

BACKGROUND OF THE INVENTION

Fluorescently labeled particles are being used in a variety of applications. By varying fluorescent dye concentration and/or the emission wavelengths of the dyes, it is possible to create an almost limitless number of fluorescently distinguishable particles. One such technology currently available uses polystyrene microspheres into which are incorporated precisely controlled quantities of two fluorescent dyes. See, for example, U.S. Pat. No. 5,981,180, granted to Chandler et al.

Once separately addressable microsphere sets have been constructed, different specific biomolecular reactions, including but not limited to, DNA, immunoassay, receptor-ligand, or enzyme-based assays, are performed on the discrete microsphere sets. When passed through a flow analyzer, the reaction can be classified by the internal microsphere fluorescent signature (i.e., by the separate spectral addresses), while the biomolecular reaction is measured using fluorescence of a different color (wavelength), i.e., the reporter signal.

However, any time laboratory samples are performed sequentially, regardless of instrument type or methodology, carryover from the previous sample(s) is always a concern. In the past, elaborate wash cycles have been performed in an attempt to solve this problem. The drawback to this "solution," however, is increased cycle time, and there is no guarantee of 100% elimination of carryover.

SUMMARY OF THE INVENTION

The present invention provides for substantially 100% elimination of carryover effects and doublets by taking advantage of the flow analyzer's capability to accurately distinguish the separately addressable microsphere sets and to precisely measure the biomolecular reaction that has occurred on the surface of the microspheres. Also, the number of microspheres measured per analyte ranges over a wide number, preferably between 1 and about 10,000. Typically, a minimum of about 100 microspheres per analyte can be analyzed to provide a reliable result. The amount or intensity of surface (or reporter) fluorescence is averaged among the about 100 pieces of data to measure the extent of the biomolecular reaction. Coefficients of variation (CV's), mean, and standard deviation can be calculated for the measured value.

The maximum number, say N, of microspheres that could ever carryover from sample to sample is physically measured and/or statistically calculated. According to a particular embodiment of the present invention, 2N+100 microspheres could be analyzed for each biomolecular reaction, yielding 2N+100 pieces of measurement data. The analysis package can then be tailored to discard N highest measured values and N lowest measured values, and average the extent of the biomolecular reaction using only the remaining 100 pieces of measurement data.

According to a preferred embodiment of the invention, only microspheres carrying surface fluorescence values plus or minus two standard deviations from the mean value would be taken into account towards the ultimate assay measurement. Microspheres from a prior sample can be expected to carry surface fluorescence values falling either inside or outside this window.

If the fluorescence values of microspheres from a previous sample fall outside this window, their contribution to the final measurement value would be substantially eliminated or minimized because enough microspheres would have been measured to account for at least about twice the maximum possible number of carryover microspheres. It should now be apparent that if only, say, a total of N microspheres would have been measured initially, a large percentage of the total could be have due to carryover microspheres. The resulting CV's, mean, and standard deviation values would then have been greatly influenced by the surface fluorescence values of such carryover microspheres. The ultimate reading, then, would have been erroneous.

Of course, if the carryover values fall inside the window, these carryover values would be taken into account; however, these carryover values would not change the result for the particular sample of interest.

In other words, carryover effects that could have altered the biomolecular result would have been eliminated. In addition, any doublets, which would have displayed approximately twice the surface fluorescence values of a single microsphere and, hence, could have erroneously influenced the biomolecular measurement, would have been eliminated.

In much the same manner, the maximum number of particles that could potentially be misclassified (despite the unique spectral address of microspheres in a subset) could be determined. As many "extra" microspheres could then be analyzed to negate any possible effect the misclassified microspheres might have on the assay results.

Accordingly, the present invention provides a method of reducing flow analysis error in at least one assay comprising: (a) passing a population of one or more subsets of spectrally addressable microspheres, which had been exposed to a sample suspected of harboring one or more analytes of interest, through a flow analyzer, each subset of spectrally addressable microspheres being distinguishable by at least one characteristic from at least one other subset of spectrally addressable microspheres, said microspheres exhibiting a surface fluorescence value indicative of a biomolecular reaction having taken place on the surface of said microspheres in the presence of said one or more analytes of interest; (b) discarding a number of highest surface fluorescence values and a number of lowest surface fluorescence values, which number equals a maximum number of microspheres, N, carried over from a prior assay; and (c) calculating the extent of the biomolecular reaction, if any, based on the remaining, undiscarded surface fluorescence values. In preferred embodiments of the invention, the method further comprises determining at least the coefficients of variation, mean, and standard deviation of the surface fluorescence values. What is more the calculation of the extent of the biomolecular reaction is carried out only one those remaining, undiscarded surface fluorescence values that are within two standard deviations of the mean.

Consistent with the objectives of the present invention, the number N is predetermined or estimated. An approximate minimum number, M, of microspheres required to afford a reliable assay can also be determined or estimated. Preferably, in the assay of the present invention at least about 2N+M microspheres are passed through the flow analyzer, more preferably at least about 2(N+M). Most preferred assays are those which comprise a multiplexed assay, in which multiple analytes are determined substantially simultaneously.

In another object of the invention a method is provided of reducing microsphere misclassification error in at least one assay comprising the steps of: (a) passing a population of one or more subsets of spectrally addressable microspheres through a flow analyzer, each subset of spectrally addressable microspheres being distinguishable by at least one characteristic from at least one other subset of spectrally addressable microspheres, said at least one characteristic expressed as a certain value measurable by the flow analyzer; (b) discarding a number of highest values and a number of lowest values, which number equals a maximum number of microspheres, N', which can be misclassified; and (c) determining the classification of the one or more subsets of microspheres based on the remaining, undiscarded values. The source of microspheres, which can be misclassified, comprises microspheres carried over from one or more prior assays or comprises microspheres present in the at least one assay.

The following example is provided as a further illustration of the invention.

EXAMPLE

An aliquot of microspheres, containing about 200 to about 500 particles per aliquot and which has been exposed to a first sample, is run through a flow analyzer and measurements are carried out as usual. A "dummy" aliquot (containing no microspheres) is then exposed to a second sample and subsequently loaded onto the flow analyzer. A "dummy" measurement is carried out. In this "dummy" measurement, only microspheres from the prior sample will be detected and physically counted by the instrument. Further "dummy" experiments are then run until no carryover microspheres are detected. These experiments are repeated using varying amounts (numbers) of microspheres in test aliquots. A maximum number of carryover microspheres can then be estimated for any subsequent runs based on the initial amounts (numbers) of microspheres loaded from prior experiments.

Hence, if the maximum number of carryover microspheres is determined to be, say, about 20, and it is determined that a minimum number of microspheres required to produce a reliable measurement figure is about 300, then a minimum of 2(20)+300 or 340 microspheres is measured in subsequent runs. The 20 highest values are discarded (eliminating carryover values above the mean value of the current run). The 20 lowest values are discarded (eliminating carryover values below the mean value of the current run). If desired, only those values of the remaining 300 values, which are within two standard deviations of the mean, are taken into account towards the ultimate calculation of the extent of the biomolecular reaction. In this case, perhaps 400 microspheres might be measured to provide for sufficient numbers of qualifying measurements.

During multiplexed analyses, many subsets of microspheres might be in use, thus greatly increasing the absolute numbers of microspheres in use to, e.g., thousands. The principles described herein would still apply, however, as would be evident to one of ordinary skill in the art. In particular, the unique spectral address of microspheres belonging to a particular subset can be exploited so that individual measurements and calculations can be performed, which are selectively directed to potential carryover problems associated with a particular subset.

What is claimed is:

1. A method of reducing flow analysis error in at least one flow analysis assay on a flow analyzer, wherein said flow analysis assay is performed subsequent to at least one prior flow analysis assay performed on the same flow analyzer, comprising:

a) passing a population of one or more subsets of spectrally addressable microspheres, which had been exposed to a sample suspected of harboring one or more analytes of interest, through a flow analyzer, each subset of spectrally addressable microspheres being distinguishable by at least one characteristic from at least one other subset of spectrally addressable microspheres, said microspheres exhibiting a surface fluorescence value indicative of a biomolecular reaction having taken place on the surface of said microspheres in the presence of said one or more analytes of interest;

b) discarding a number, N, of highest surface fluorescence values and a number, N, of lowest surface fluorescence values, which number equals a maximum number of microspheres, N, carried over from said prior assay performed on said same flow analyzer; and c) calculating the extent of the biomolecular reaction, if any, using surface fluorescence values not discarded in step b).

2. The method of claim 1 which further comprises determining coefficients of variation, mean, and standard deviation of the surface fluorescence values not discarded in step b).

3. The method of claim 2 in which the calculation of the extent of the biomolecular reaction is carried out only on those surface fluorescence values not discarded in step b that are within two standard deviations of the mean.

4. The method of claim 1 in which N is predetermined or estimated by a method comprising:

a. passing a first sample comprising a known quantity of microspheres through a flow analyzer;

b. passing a second sample comprising no microspheres through said flow analyzer; and c. calculating the number of microspheres detected by the flow analyzer in said second sample, wherein N, the maximum number of microspheres carried over from a prior assay, is the number of microspheres detected in the second sample.

5. The method of claim 4 in which a minimum number, M, of microspheres required to produce an assay having a low flow analysis error is estimated.

6. The method of claim 5 in which at least about 2N+M microspheres are passed through the flow analyzer.

7. The method of claim 1 which comprises a multiplexed assay.

* * * * *